United States Patent [19]

Allison et al.

[11] Patent Number: 4,770,874

[45] Date of Patent: Sep. 13, 1988

[54] POLYOXYPROPYLENE-POLYOXYETHYLENE BLOCK POLYMER BASED ADJUVANTS

[75] Inventors: Anthony C. Allison, Belmont; Noelene E. Byars, Sunnyvale, both of Calif.

[73] Assignee: Syntex (U.S.A.) Inc., Palo Alto, Calif.

[21] Appl. No.: 859,665

[22] Filed: May 5, 1986

Related U.S. Application Data

[62] Division of Ser. No. 525,190, Aug. 22, 1983, Pat. No. 4,606,918.

[51] Int. Cl.$^4$ .............................................. A61K 39/39
[52] U.S. Cl. ..................................... 424/88; 424/85; 424/86; 424/87; 424/88; 424/89; 424/90; 424/91; 424/92; 514/8; 514/885; 436/543; 530/322; 530/806; 530/815; 252/351; 252/352
[58] Field of Search .................................. 424/85–92; 514/8, 885; 436/543; 530/322, 806, 815; 252/351–352

[56] References Cited

U.S. PATENT DOCUMENTS

| | | | |
|---|---|---|---|
| 3,867,521 | 2/1975 | Miskel et al. | 424/78 |
| 3,869,546 | 3/1975 | Lund | 424/88 |
| 3,869,549 | 3/1975 | Geller | 514/12 |
| 3,919,411 | 11/1975 | Glass et al. | 424/88 |
| 4,082,735 | 4/1978 | Jones et al. | 536/53 |
| 4,082,736 | 4/1978 | Jones et al. | 536/53 |
| 4,101,536 | 7/1978 | Yamamura et al. | 514/8 |
| 4,148,869 | 4/1979 | Deaton | 424/1.1 |
| 4,158,052 | 6/1979 | Audibert et al. | 424/88 |
| 4,185,089 | 1/1980 | Derrein et al. | 424/88 |
| 4,220,637 | 9/1980 | Audibert et al. | 424/88 |
| 4,314,998 | 2/1982 | Yamamura et al. | 424/88 |
| 4,323,559 | 4/1982 | Audibert et al. | 514/12 |
| 4,323,560 | 6/1982 | Baschang et al. | 424/88 |
| 4,369,178 | 1/1983 | Yamamura et al. | 514/8 |
| 4,382,080 | 5/1983 | Shiba et al. | 514/8 |
| 4,384,974 | 5/1983 | Guthauser et al. | 252/309 |
| 4,397,870 | 8/1983 | Sloviter | 514/672 |
| 4,406,889 | 9/1983 | Hartmann et al. | 424/88 |
| 4,409,209 | 10/1983 | Baschang et al. | 514/12 |
| 4,423,038 | 12/1983 | Baschang et al. | 514/8 |
| 4,427,659 | 1/1984 | Le Francier et al. | 514/8 |
| 4,461,761 | 7/1984 | Le Francier et al. | 514/8 |
| 4,578,269 | 3/1986 | Morein et al. | 424/88 |

FOREIGN PATENT DOCUMENTS

3308458-A 9/1984 Fed. Rep. of Germany .

OTHER PUBLICATIONS

Dukor et al, Annual Reports in Medicinal Chemistry–14, Chapter 15 (Immunostimulants) pp. 1416–1467.
Hunter, et al., *J. Immunol.*, 127, 1244 (1981).
Hunter, et al., Rev. Cancer Res., 3, 279–286 (1980).
Snippe, et al., Int. Archs. Allergy Appl. Immun., 65, 390–398 (1981).

*Primary Examiner*—John Kight
*Assistant Examiner*—Garnette D. Draper
*Attorney, Agent, or Firm*—Carol J. Roth; Tom M. Moran

[57] ABSTRACT

An adjuvant composition contains an immunopotentiating amount of an immunostimulating glycopeptide, a polyoxypropylene-polyoxyethylene block polymer, a glycol ether-based surfactant, and, optionally, a metabolizable non-toxic oil.

16 Claims, No Drawings

POLYOXYPROPYLENE-POLYOXYETHYLENE BLOCK POLYMER BASED ADJUVANTS

This is a division of pending application Ser. No. 525,190, filed Aug. 22, 1983, now U.S. Pat. No. 4,606,918 incorporated herein by reference.

BACKGROUND OF THE INVENTION

This invention relates to adjuvants and vaccines. More particularly, this invention relates to adjuvants and vaccines based on polyoxypropylene-polyoxyethylene block polymers.

Freund's discovery that the immunogenicity of antigens could be potentiated by emulsifying an aqueous antigen solution with mineral oil alone or with mineral oil and *M. tuberculosis*, formed the basis of the concept of using a secondary material to increase a subject's humoral and cell-mediated immune responses to an antigen. An essential component of Freund's complete and incomplete adjuvant is mineral oil. This component plays a central role in effecting an increased humoral response to the antigen. However, mineral oil is only acceptable for use in research circumstances. The mycobacteria in complete Freund's adjuvant are essential for significantly enhanced cellular immunity.

Though little attention was initially paid to the role that surfactant may play in Freund's incomplete or complete adjuvant, subsequent research has indicated that in several instances a surfactant may demonstrate adjuvant properties in and of itself. A number of naturally occurring surface active agents such as the lipid A portion of endotoxin of gram negative bacteria and trehalose dimycolate of mycobacteria are among the most potent adjuvants of these naturally occurring surfactants. A constituent of mammalian cells, the phospholipid lysolecithin also has been shown to have adjuvant activity. (B. Arnold et al, *Eur. J. Immunol.*, 9: 363-366 (1979).)

In addition, several synthetic surfactants, for example, dimethyldioctadecyl ammonium bromide (DDA) and certain polyoxypropylene-polyoxyethylene block polymers have been reported as having adjuvant activity. (See H. Snippe et al, *Int. Archs. Allergy Appl. Immun.*, 65: 390-398 (1981). In addition, R. Hunter et al, have reported in the *Journal of Immunology*, 127: 1244-1250 that polyoxypropylene-polyoxyethylene block polymers, when used as the surfactant component of an oil-in water based adjuvant formulation, increase antibody formation to BSA in mice.

While there natural and synthetic surfactants demonstrate a certain degree of adjuvanticity, results so far published demonstrate that, except for one specific test methodology for DDA, none of the surfactants when used alone matches the immunopotentiating activity found when using complete or incomplete Freund's adjuvant. However, it is not possible to use either Freund's incomplete or complete adjuvant for general vaccination purposes because both mineral oil and mycobacteria have deleterious side effects when injected subcutaneously as a result of which it has not been authorized for domestic animal or human use by governmental regulatory agencies. Mineral oil is limited to use in experimental animals.

However, there is a substantial need for some means of potentiating the immunogenicity of antigens. This is particularly true because virus subunit and other protein antigens are now being prepared by recombinant DNA technology. Moreover, naturally occurring or synthetic peptide fragments from larger proteins known to be antigenic are being administered rather than whole protein or a mixture of materials containing the whole protein.

To elicit useful immune responses, antigenic proteins and haptens must be administered with some type of adjuvant. Neither mineral oil nor mycobacteria can be used, as noted above. Glycopeptides should be able to provide the needed immunopotentiation, but these materials are most effective when presented to the subject as an emulsion. Since mineral oil may not be used due to its toxicity, an alternative emulsion-forming material is need for administering antigens.

It has now been found that when immunopotentiating glycopeptides and an antigen are confected with a non-toxic polyoxypropylene-polyoxyethylene block polymers and a multiphase stabilizing amount of a glycol ether-based non-toxic surfactant, the immunogenicity of the antigen is increased in the same manner and to the same degree as when mineral oil is used. It has been found that the block polymer is critical to achieving an immune response but that a maximal response to most effectively achieved only when the multiphase system is stabilized by some detergent such as a non-ionic glycol ether-based surfactant. The presence of a metabolizable oil may enhance the effectiveness of these formulations as well. Because the polyoxypropylene-polyoxyethylene block polymers and glycol ether surfactants are non-toxic, this adjuvant formulation may be safety used as a vehicle for enhancing the immunogenicity of antigens administered to birds and mammals.

SUMMARY OF THE INVENTION

This invention is drawn to an adjuvant vehicle for vaccines comprising an immunopotentiating amount of glycopeptide, a multiphase-forming amount of a non-toxic polyoxypropylene-polyoxyethylene block copolymer, a multiphase-stabilizing amount of a glycol ether-based surfactant, optionally a metabolizable oil of 6 to 30 carbon atoms, and buffered, isoosmotic aqueous solution in a quantity sufficient to make volume.

In a second aspect, this invention relates to a vaccine composition comprising an effective amount of an antigen, an immunopotentiating amount of a glycopeptide, a multiphase-forming amount of a non-toxic polyoxypropylene-polyoxyethylene block copolymer, a multiphase-stabilizing amount of a glycol ether-based surfactant, optionally a metabolizable oil of 6 to 30 carbon atoms, and buffered, isoosmotic aqueous solution in a quantity sufficient to make volume.

In yet another aspect, this invention relates to a method for enhancing the immunogenicity of an antigen which method comprises emulsifying an antigen with an adjuvant vehicle comprising an immunopotentiating amount of glycopeptide, a multi-phase forming amount of a non-toxic polyoxypropylene-polyoxyethylene block copolymer, a multiphase-stabilizing amount of a glycol ether-based surfactant, optionally a metabolizable oil of 6 to 30 carbon atoms, and buffered, isoosmotic aqueous solution in a quantity sufficient to make volume and administering said emulsion to a bird or mammal.

DETAILED DESCRIPTION OF THE INVENTION

As pointed out hereinabove the uniqueness of this invention lies in the use of polyoxypropylene-polyoxyethylene block copolymers in combination with a second surfactant such as a glycol ether-based surfactant as an adjuvant vehicle which, when formed into an emulsion with an immunopotentiating glycopeptide and an antigen, potentiates the immunogenicity of an antigen. This formulation is further unique in that it represents a formulation which can be safely administered to birds and mammals. Thus it is possible to prepare injectible vaccines wherein the antigen will elicit humoral and cell mediated immune responses comparable with those that can be obtained if the antigen was administered in Freund's incomplete or complete adjuvant. A vaccine with such properties will serve to reduce the number of times an antigen must be administered in order to develop a protective response in the subject. In addition, the amount of antigen needed to be administered to elicit a protective response can be reduced.

The polyoxypropylene-polyoxyethylene (POP-POE) block copolymers of this invention are a widely available material commercially known the by trademark Pluronic ® polyols. These compounds are made by the sequential addition of propylene oxide and then ethylene oxide to a low molecular weight, reactive hydrogen compound, usually propylene glycol. The characteristics of these polyols are determined by the molecular weight of the polyoxyethylene glycol nucleus and of the ratio of polyoxypropylene to polyoxyethylene in the product. Polyoxypropylene glycols with a molecular weight of approximately 900 or more are water insoluble and impart hydrophobic characteristics to the polyol. The polyethylene glycol, which usually constitutes from approximately 10% to 90% of the total weight, imparts water-soluble properties to the polymer, thus resulting in a compound having surface active properties.

POP-POE block polymers may be represented empirically by the formula:

$$HO(CH_2CH_2O)_a(\underset{\displaystyle CH_3}{\underset{|}{C}}HCH_2O)_b(CH_2CH_2O)_cH$$

wherein a and c are statistically equal. These compounds can be prepared by the methods set out in U.S. Pat. No. 2,674,619 issued to Lunsted. The most common means of making the compound is to react a bifunctional initiator, propylene glycol, with propylene oxide in the presence of a catalytic amount of anhydrous sodium hydroxide and the reaction allowed to proceed until the desired molecular weight is obtained. A set amount of ethylene oxide is then added to the same reaction pot to make the block copolymer.

These block polymer polyols range in molecular weight from approximately 1,000 up to 16,000. The polymers of particular interest to this invention are those having an average molecular weight between about 5,000 and 15,500. Such materials are commercially available from several sources, for example, BASF-Wyandotte Corp., Parsippany NJ. 07054 and E. I. Du pont.

POP-POE polyols available from BASF-Wyandotte under the name Pluronic ® are identified by a letter prefix followed by a two or a three digit number. The letter prefixes are L, P and F and refer to the physical form of each polymer, L-liquid, P-paste, or F-flakeable solid. The two and three digit numbers are used to designate the average molecular weight of the polyoxypropylene hydrophobic base in comparison with the percent polyoxyethylene in the total molecule. Take, for example, PLURONIC ® L-101. The first two digits refer to the fact the polyoxypropylene base has a typical molecular weight of 3,250 while the third digit indicates 10% polyoxyethylene is present in the polymer. A second example would be PLURONIC ® F-108. Here, again, the "10" designates a polyoxypropylene base which has a typical molecular of 3,250 while the "8" designates that polyoxyethylene comprises 80% of the total molecule.

The block polymers of greatest interest to this invention are those which are liquid over a temperature range between about 15°–40° C. In addition, polymer mixtures of liquid and paste, liquid, paste and flakeable solid or liquid and flakeable solid mixtures which are liquid within the specified temperature range may have utility in this invention.

Preferred block polymers are those having a POP base ranging in molecular weight between about 2250 and 4300 and POE in an amount between about 1 and 30%. More preferred are those polymers wherein POP has a molecular weight falling between 3250 and 4000 and the POE component comprises 10–20%. The PLURONIC ® polyols L-101, L-121 and L-122 fall within this definition. Most preferred are the polymers wherein POP has a molecular weight of 4000 and POE in an amount of 10% or POP has a molecular weight of 3250 and POE in an amount of 10% eg. PLURONIC ® polyols L-121 and L-101 respectively.

A multi-phase forming amount of polymer is that quantity which will form micelles, or more broadly, a system characterized as an emulsion or suspension. For the purposes of this invention that is some amount between 0.2% and 49% by volume. A more preferred amount would be between 0.2% and 20% (V/V) though up to 5% is even more preferred and 2.5% is most preferred.

The efficacy of these compositions can best be realized by employing a non-toxic, non-ionic detergent to stabilize the formed multi-phase composition. If the block polymer alone is used, the antigen will show some increased immunogenicity but the effect will be smaller in comparison with the effect observed when the non-ionic detergent is present. This non-ionic detergent could also be characterized as an emulsifying or suspending agnet in that it is present for achieving those two purposes and is present in a minor amount in comparison to the block polymer, which could be characterized as the "oil" in the compositions of this invention.

There are a substantial number of emulsifying and suspending agents generally used in the pharmaceutical sciences. There are naturally derived materials such as gums from trees, vegetable protein, sugar-based polymers such as alginates and cellulose, and the like. Certain oxypolymers or polymers having an hydroxide or other water soluble substituent substituted on the carbon backbone have surfactant activity, for example, povidone, polyvinyl alcohol, and glycol ether-based mono- and poly-functional compounds. Long chain fatty acid-derived compounds form a third substantial group of emulsifying and suspending agents which could be used in this invention. Though any of the foregoing surfactants could be used so long as they are non-toxic, the glycol ether derived compounds are the emulsifying agents of choice in this invention.

The simplest member of the family of compounds based on the glycol ethers is ethylene oxide. The internal or cyclic ethers of the simplest glycol, ethylene glycol, mono- and diethers of ethylene glycol are also well-known. One important group of glycol ethers is the polyethylene glycols. The compounds of most interest herein are the PEG 200, 300, 400, 600 and 900.

A particularly useful group of surfactants are the sorbitan-based non-ionic surfactants. These surfactants are prepared by dehydration of sorbitol to give 1,4-sorbitan which is then reacted with one or more equivalents of fatty acid or the fatty acid substituted moiety is further reacted with ethylene oxide to give a second group of surfactants.

The fatty acid substituted sorbitan surfactants are made by reacting 1,4-sorbitan with a fatty acid such as lauric acid, palmitic acid, stearic acid, oleic acid, or a similar long chain fatty acid to give the 1,4-sorbitan mono-ester, 1,4-sorbitan sesquiester or 1,4-sorbitan triester. The common name for these surfactants are for example sorbitan monolaurate, sorbitan monopalmitate, sorbitan monostearate, sorbitan monooleate, sorbitan sesquioleate, sorbitan trioleate. These surfactants are commercially available under the name SPAN® or ARLACEL®, usually with a letter or number designation which distinguishes between the various mono-, di- and triester substituted sorbitans.

SPAN® and ARLACEL® surfactants are hydrophilic and are generally soluble or dispersible in oil and tend to form water-in-oil emulsions. They are also soluble in most organic solvents. In water they are generally insoluble but dispersible. Generally these surfactants will have a hydrophilic-lipophilic balance (HLB) number between about 1.8 to 8.6. Such surfactants can be readily made by means known in the art or are commercially available from, for example, ICI, America's Inc., Wilmington, Del. under the registered mark ATLAS®.

A related group of surfactants are the polyoxyethylene sorbitan monoesters and polyoxyethylene sorbitan triesters. These materials are prepared by addition of ethylene oxide to a 1,4-sorbitan monoester or triester. The addition of polyoxyethylene converts the lipophilic sorbitan mono- or triester surfactant to a hydrophilic surfactant generally soluble or dispersible in water and soluble in varying degrees in organic liquids.

These materials, commercially available under the mark TWEEN®, are useful for preparing oil-in-water emulsions, dispersions or for the solubilization of oils and making anhydrous ointments water-soluble or washable. The TWEEN® surfactants may be combined with a related sorbitan monoester or triester surfactants to promote emulsion stability. TWEEN® surfactants generally have a HLB value falling between 9.6 to 16.7. TWEEN® surfactants are commercially available from a number of manufacturers for example ICI, America's Inc., Wilmington, Del. under the registered mark ATLAS® surfactants.

A third group of non-ionic surfactants which could be used alone or in conjunction with SPAN®, ARLACEL® and TWEEN® surfactants are the polyoxyethylene fatty acids made by the reaction of ethylene oxide with a long-chain fatty acid. The most commonly available surfactant of this type is sold under the name MYRJ® and is a polyoxyethylene derivative of stearic acid. MYRJ® surfactants are hydrophilic and soluble or dispersible in water like TWEEN® surfactants. The MYRJ® surfactants may be blended with TWEEN® surfactants or with TWEEN®/SPAN® or ARLACEL® surfactant mixtures for use in forming emulsions. MYRJ® surfactants can be made by methods known in the art or are available commercially from ICI America's Inc.

A fourth group of polyoxyethylene based non-ionic surfactants are the polyoxyethylene fatty acid ethers derived from lauryl, acetyl, stearyl and oleyl alcohols. These materials are prepared as before by addition of ethylene oxide to a fatty alcohol. The commercial name for these surfactants is BRIJ®. BRIJ® surfactants may be hydrophilic or lipophilic depending on the size of the polyoxyethylene moiety in the surfactant. While the preparation of these compounds is available from the art, they are also readily available from such commercial sources as ICI America's Inc.

Other non-ionic surfactants which potentially could be used in the practice of this invention are for example: polyoxyethylene, polyol fatty acid esters, polyoxyethylene ether, polyoxypropylene fatty ethers, bee's wax derivatives containing polyoxyethylene, polyoxyethylene lanolin derivatives, polyoxyethylene fatty glycerides, glycerol fatty acid esters or other polyoxyethylene acid alcohol or ether derivatives of long-chain fatty acids of 12–21 carbon atoms.

As the adjuvant and the vaccine formulations of this invention are intended to be multi-phase systems, it is preferable to choose an emulsion-forming non-ionic surfactant which has an HLB value in the range of about 7 to 16. This value may be obtained through the use of a single non-ionic surfactant such as a TWEEN® surfactant or may be achieved by the use of a blend of surfactants such as with a sorbitan mono-, di- or triester with a compatible polyoxyethylene sorbitan mono- or triester based surfactant; a sorbitan ester-polyoxyethylene fatty acid; a sorbitan ester in combination with a polyoxyethylene lanolin derived surfactant; a sorbitan ester surfactant in combination with a high HLB polyoxyethylene fatty ether surfactant; or a polyethylene fatty ether surfactant or polyoxyethylene sorbitan fatty acid.

It is more preferred to use a single non-ionic surfactant, most particularly a TWEEN® surfactant, as the emulsion stabilizing non-ionic surfactant in the practice of this invention. Most preferably the surfactant named TWEEN® 80 otherwise known as polysorbate 80 for polyoxyethylene 20 sorbitan monooleate is the most preferred of the foregoing surfactants.

Multiphase stabilization usually can be effected by having the surfactant present in an amount of 0.05 to 2.5% by weight (w/v) or volume (v/v), depending on whether the material is a solid or liquid at room temperature. An amount of 0.2% to 1% is preferred.

The immune response stimulating glycopeptides of this invention are a group of compounds related to and derived from the N-acetylmuramyl-L-alanyl-D-isoglutamine, which was determined by Ellouz et al, *Biochem. & Biophys. Res. Comm.*, Vol. 59, 4, 1317 (1974) to be the smallest effective unit possessing immunological adjuvant activity in [M. tuberculosis, the mycobacterial component of Freund's complete adjuvant. A number of dipeptide- and polypeptide-substituted muramic acid derivatives were subsequently developed and found to have immunostimulating activity.

Though these glycopeptides are a diverse group of compounds, they can be generally represented by the formula

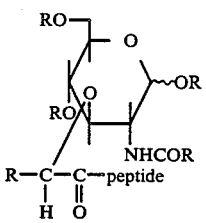

wherein the pyran ring oxygens are substituted by hydrogen, alkyl, or acyl or the like, or may be replaced by nitrogen-based substituent, particularly the 6-position oxygen; the 2-amino group is an acyl group or some other amide, the lactyl side chain is modified, i.e. is ethyl or another two-position alkyl moiety; and the peptide function is a dipeptide or polypeptide. Furanosyl analogs of the pyranosyl compounds also have immunopotentiating activity and are useful in this invention.

Among the glycopeptides of this invention are those disaccharides and tetrasaccharides linked by meso-$\alpha$-$\epsilon$-diaminopimelic acid such as described in U.S. Pat. Nos. 4,235,771 and 4,186,194.

Immune response stimulating glycopeptides which may be used in the practice of this invention are disclosed in U.S. Pat. Nos. 4,094,971; 4,101,536; 4,153,684; 4,235,771; 4,323,559; 4,327,085; 4,185,089; 4,082,736; 4,369,178, 4,314,998 and 4,082,735; and 4,186,194. The glycopeptides disclosed in these patents are incorporated herein by reference and made a part hereof as if set out in full herein. The compounds of Japanese patent applications Nos. J5 4079-227, J5 4079-228, J5 41206-696 and JA-028012 would also be useful in the practice of this invention.

Methods for preparing these compounds are disclosed and well-known in the art. Preparative process exemplification can be found in U.S. Pat. Nos. 4,082,736 and 4,082,735. Additional, similar preparative processes may be found in the U.S. patents referenced in the preceding paragraph.

Preferred glycopeptides are those having the Formula

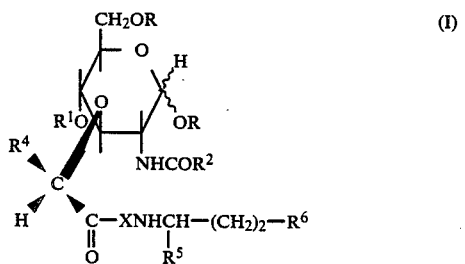

(I)

wherein R and $R^1$ are the same or different and are hydrogen or an acyl radical containing from 1 to 22 carbon atoms;

$R^2$ is an unsubstituted or substituted alkyl radical containing from 1 to 22 carbon atoms, or an unsubstituted or substituted aryl radical containing from 6 to 10 carbon atoms;

$R^3$ is hydrogen, alkyl, or aryl of 7 to 10 carbon atoms;

$R^4$ is hydrogen or alkyl of 1 to 6 carbon atoms;

X is an aminoacyl moiety selected from the group consisting of alanyl, valyl, leucyl, isoleucyl, $\alpha$-aminobutyryl, threonyl, methionyl, cysteinyl, glutamyl, glutaminyl, aspartyl, phenylalanyl, tyrosyl, tryptophanyl, lysyl, ornithinyl, arginyl, histidyl, asparaginyl, prolyl, hydroxyprolyl, seryl, or glycyl;

$R^5$ denotes an optionally esterified or amidated carboxyl group; and $R^6$ denotes an optionally esterified or amidated carboxyl group;

Alkyl is a straight or branched radical comprised of 1 to 7 carbon atoms exemplified by methyl, ethyl, propyl, butyl, pentyl, hexyl or heptyl or and isomer. Lower alkyl is a radical of 1 to 4 carbon atoms.

An optionally substituted benzyl radical is that benzyl radical which is optionally mono-substituted, di-substituted, or poly-substituted in the aromatic nucleus, for example, by lower alkyl, free, etherified or esterified hydroxyl or mercapto groups, for example, lower alkoxy or lower alkylene dioxy groups, as well as lower alkyl mercapto or trifluoromethyl groups and/or halogen atoms.

An optionally esterified or amidated carboxyl group is, the carboxyl group itself or a carboxyl group esterified with a lower alkanol, such as methanol, ethanol, propanol, butanol, or the carbamoyl group, which, on the nitrogen atom, is unsubstituted or mono-substituted or di-substituted by alkyl, especially lower alkyl, aryl, particularly phenyl, or aralkyl, particularly benzyl. The carbamoyl group may also be substituted with an alkylidene radical such as butylidene or pentylidene radical. In addition, the carbamoyl group $R_5$ may also be substituted with a carbamoylmethyl group on the nitrogen atom.

Particularly preferred compounds are those of Formula 1 wherein R and $R^1$ are the same or different and are selected from the group consisting of hydrogen or an acyl radical containing from 1 to 22 carbon atoms; $R^2$ is methyl; $R^3$ is hydrogen; X is an aminoacyl moiety selected from the group consisting of L-seryl, L-alanyl, L-valyl, L-leucyl, L-isoleucyl, L-$\alpha$-aminobutyryl, L-seryl, L-threonyl, L-methionyl, L-cysteinyl, L-phenylalanyl, L-tyrosyl, L-tryptophanyl, L-lysyl, L-ornithyl, L-arginyl, L-histidyl, L-glutamyl, L-glutamanyl, L-aspartyl, L-asparaginyl, L-prolyl, or L-hydroxyprolyl:

A more preferred group of glycopeptides are the compounds of Formula 1 wherein R, $R^1$ are hydrogen or acyl of 1 to 22 carbon atoms, $R^2$ is hydrogen, $R^3$ and $R^4$ are methyl, and X is L-valyl, L-seryl, L-alanyl, L-threonyl or L-$\alpha$-aminobutyryl.

Most particularly preferred are the following compounds:

N-acetylmuramyl-L-$\alpha$-aminobutyryl-D-isoglutamine;
6-O-stearoyl-N-acetylmuramyl-L-$\alpha$-aminobutyryl-D-isoglutamine;
N-acetylmuramyl-L-threonyl-D-isoglutamine;
N-acetylmuramyl-L-valyl-D-isoglutamine;
N-acetylmuramyl-L-alanyl-D-isoglutamine;
N-acetyl-desmethylmuramyl-L-alanyl-D-isoglutamine;
n-butyl N-acetylmuramyl-L-alanyl-D-glutaminate; and
N-acetylmuramyl-L-seryl-D-isoglutamine.

An effective amount of immunostimulating glycopeptide will be that amount which effects an increase in titer level when administered in conjunction with an antigen over that titer lever observed when the glycopeptide has not been included in the adjuvant composition. As can be appreciated, each glycopeptide may have an effective dose range that may differ from the other glycopeptides. Therefore, a single dose range cannot be prescribed which will have a precise fit for each possible glycopeptide within the scope of this invention. However, as a general rule, the glycopeptide will preferably be present in an amount of between 0.01 and 2% by weight/volume (w/v). A more preferred amount is 0.01 to 1% (w/v).

Another component of these formulations, which may be present at the option of the formulator, is a metabolizable, non-toxic oil, preferably one of 6 to 30 carbon atoms including, but not limited to, alkanes, alkenes, alkynes, and their corresponding acids and alcohols, the ethers and esters thereof, and mixtures thereof. The oil may be any vegetable oil, fish oil, animal oil or synthetically prepared oil which can be metabolized by the body of the animal or bird to which the adjuvant is been administered and which is not toxic in some manner to the organism. Mineral oil and similar petroleum distillate oils are expressly excluded from this invention.

The oil component of this invention may be any long chain alkane, alkene or alkyne, or an acid or alcohol derivative thereof either as the free acid, its salt or an ester such as a mono-, di- or triester, such as the triglycerides and esters of 1,2-propanediol or similar multi-hydroxy alcohol. Alcohols may be acylated employing a mono or poly functional acid, for example acetic acid, propanoic acid, citric acid and the like. Ethers derived from long chain alcohols which are oils and meet the other criteria set forth herein may also be used.

The individual alkane, alkene or alkyne moiety and its acid or alcohol derivatives will have 6–30 carbon atoms. The moiety may have a straight or branched chain structure. It may be fully saturated or have one or more double bonds or acetylenic bonds. Where mono or poly ester- or ether-based oils are employed, the limitation of 6–30 carbons applies to the individual fatty acid or fatty alcohol moiety, not the total carbon count.

Any metabolizable oil, particularly from an animal, fish or vegetable source, may be used herein. It is essential that the oil be metabolized by the animal or bird to which it is administered, otherwise the oil component may cause abscesses, granulomas or even carcinomas, or may make the meat of vaccinated birds and animals unacceptable for human consumption because of the deleterious effect the unmetabolized oil may have on the consumer.

Nuts, seeds and grains are the sources for the so called vegetable oils. Peanut oil, soybean oil, coconut oil, and olive oil, the most commonly available, exemplify the nut oils. Seed oils include safflower oil, cottonseed oil, sunflower seed oil, sesame seed oil and the like. In the grain group, corn oil is readily available but while the oil of other cereal grains such as wheat, oats, rye, rice, triticale and the like may be used, such oils, except for wheat germ oil, are not readily available and therefore of less interest, but only for the reason cereal grain oils may be more difficult to obtain commercially.

The technology for obtaining the vegetable oils is well developed and well known. The compositions of these and other similar oils may be found in, for example, the Merck Index, and source materials on foods, nutrition and food technology.

The 6–10 carbon fatty acid esters of glycerol and 1,2-propanediol, while not occurring naturally in seed oils, may be prepared by hydrolysis, separation and esterification of the appropriate materials starting from the nut and seed oils. These products are commercially available under the name NEOBEE ® from PVO International, Inc., Chemical Specialities Division, 416 Division Street, Boongon, N.J. and others. Reference is made to U.S. patent application Ser. No. 341,403, filed Jan. 21, 1982 for methods for making these latter materials.

Oils from any animal source, including birds, may be employed in the adjuvants and vaccines of this invention. Animal oils and fats usually are solids at physiological temperatures due to the fact they exist as triglycerides and have a higher degree of saturation than oils from fish or vegetables. However, fatty acids are obtainable from animal fats by partial or complete triglyceride saponification which gives the free fatty acids. Fats and oils from mammalian milk are metabolizable and therefore could be used in the practice of this invention. The procedures for separation, purification, saponification and other means necessary for obtaining pure oils from animal sources are well known in the art.

Another source of oils are the fish oils. Most fish contain metabolizable oils which may be readily recovered. For example, cod liver oil, shark liver oils, and whale oil such as spermaceti exemplify several of the fish oils which may be used herein. Shark liver oil contains a branched, unsaturated oil known as squalene, 2,6,10,15,19,23-hexamethyl-2,6,10,14,18,22-tetracosahexaene which is particularly preferred herein. Squalane, the saturated analog of squalene is also a particularly preferred oil herein. Fish oils, including squalene and squalane, are readily available from commercial sources or may be obtained by methods known in the art.

The oil component of these adjuvants and vaccine formulations will be present in an amount between 1 to 30% by volume/volume but preferably in an amount of 1 to 10% v/v. It is most preferred to use a 5% v/v concentration of oil.

The aqueous portion of these adjuvant compositions is buffered, isoosmotic saline. Because these compositions are intended for parenteral administration, it is preferable to make up these solutions so that the tonicity, i.e., osmololality, is essentially the same as normal physiological fluids in order to prevent post-administration swelling or rapid absorption of the composition because of differential ion concentrations between composition and physiological fluids. It is also preferable to buffer the saline in order to maintain a pH compatible with normal physiological conditions. Also, in certain instances, it may be necessary to maintain the pH at a particular level in order to insure the stability of certain composition components, such as the glycopeptides.

Any physiologically acceptable buffer may be used herein but it has been found that it is most convenient to use a phosphate buffer. Any other acceptable buffer such as acetate, tris, bicarbonate, carbonate, or the like could be used as a substitute for a phosphate buffer.

The pH of the aqueous component will preferably be between 6.0–8.0 though it is preferable to adjust the pH of the system to 6.8 where that pH is compatible with maintaining the stability of other composition components or for any other physiologically suitable reason.

The quantity of buffered saline employed in these compositions will be that amount necessary to bring the value of the composition to unity. That is, a quantity of buffered saline sufficient to make 100% will be mixed in with the other components listed hereinabove in order to bring the solution to volume.

The word antigen refers to any substance, usually a protein or protein-polysaccharide, protein-lipopolysacchride, polysaccharide or lipopolysaccharide which, when foreign to the blood stream of a bird or animal, on gaining access to the tissue of such an animal, stimulates the formation of specific antibodies and reacts specifically in vivo or in vitro with an homologous antibody. Moreover, it stimulates the proliferation of T-lymphocytes with receptors for the antigen, and can react with the lymphocytes to initiate the series of responses designated cell-mediated immunity.

A hapten is within the scope of this definition. A hapten is that portion of an antigenic molecule or antigenic complex that determines its immunological specificity. Commonly, a hapten is a peptide or polysaccharide in naturally occurring antigens. In artificial antigens it may be a low molecular weight substance such as, for example, an arsanilic acid derivative. A hapten will react specifically in vivo and in vitro with homologous antibodies or T-lymphocytes. Alternative descriptors are antigenic determinant, antigenic structural grouping and haptenic grouping.

The formulation of a vaccine using the adjuvant compositions described herein will employ an effective amount of antigenic material. That is, there will be included an amount of antigen which, in combination with the adjuvants, will cause the subject to produce a specific and sufficient immunological response so as to impart protection to the subject to the subsequent exposure to the material or organism against which the vaccine is intended to be effective. Alternatively, the antibody will combine with a hormone or naturally occurring material in such a way as to alter biological processes such as growth.

No single dose designation can be assigned which will provide specific guidance for each and every antigen which may be employed in this invention. The effective amount of antigen will obviously be a factor of its inherent activity and molecular weight and will be a function of the degree to which the specific antigen can be purified from its source. It is contemplated that the adjuvant compositions of this invention may be used in conjunction with whole cell or virus vaccines as well as purified antigens or subunit or peptide vaccines prepared by recombinant DNA techniques or synthesis.

Adjuvant preparations are readily made by well known art methods. For example, one can make a 2-fold concentrated solution of the antigen and glycopeptide in the buffered saline. A two-fold concentration of the block polymer, oil, and multiphase stabilizing surfactant is mixed with buffered saline and sonicated; then the first and second solution are mixed and sonicated.

A further understanding of the invention may be had from the following non-limiting examples.

EXAMPLE 1

The activity of the adjuvant compositions was examined by means of a delayed hypersensitivity test and by an egg albumin (EA) antibody production test in guinea pigs. These two assays measure the ability of the adjuvant compositions to stimulate delayed hypersensitivity (DH, cell mediated response) and antibody synthesis (Ab, humoral immune response) in response to specific antigens in guinea pigs. The two tests were as follows: groups of 8 female guinea pigs were injected subcutaneously with EA emulsified in the adjuvant composition. Appropriate controls were included. The animals were subsequently skin tested with EA to measure delayed hypersensitivity, and were bled to obtain serum for antibody titrations.

Standard bioassay procedures were set up as follows: EA (200 micrograms per animal) was dissolved in saline and then emulsified with each of the six following adjuvant compositions.

TABLE 1

First Test Composition

| Components | Quantity |
|---|---|
| N—acetylmuramyl-L-threonyl-D-Isoglutamine | 250 μg |
| TWEEN ® 80 | 2 μl |
| PLURONIC ® L-121 | 25 μl |
| Squalene | 50 μl |
| Phosphate buffered saline QS | 1000 μl |

TABLE 2

Second Test Compositon

| Components | Quantity |
|---|---|
| N—acetylmuramyl-L-threonyl-D-Isoglutamine | 250 μg |
| TWEEN ® 80 | 2 μl |
| PLURONIC ® L 121 | 25 μl |
| Phosphate buffered saline QS | 1,000 μl |

TABLE 3

Third Test Composition

| Components | Quantity |
|---|---|
| N—acetylmuramyl-L-threonyl-D-Isoglutamine | 250 μg |
| TWEEN ® 80 | 2 μl |
| Squalene | 50 μl |
| Phosphate buffered saline QS | 1,000 μl |

TABLE 4

Fourth Test Composition

| Components | Quantity |
|---|---|
| N—acetylmuramyl-L-threonyl-D-Isoglutamine | 250 μg |
| PLURONIC ® L-121 | 25 μl |
| Squalene | 50 μl |
| Phosphate buffered saline QS | 1,000 μl |

TABLE 5

Fifth Test Composition

| Components | Quantity |
|---|---|
| PLURONIC ® L-121 | 250 μl |
| Squalene | 50 μl |
| Phosphate buffered saline QS | 1,000 μl |

TABLE 6

Sixth Test Composition

| Components | Quantity |
|---|---|
| N—acetylmuramyl-L-threonyl-D-Isoglutamine | 250 μg |
| PLURONIC ® L 121 | 25 μl |
| Phosphate buffered saline QS | 1,000 μl |

0.2 ml of this emulsion were administered per guinea pig. A booster injection of egg albumin in saline was given at 4 weeks. Blood samples were drawn at three and six weeks to determine EA antibody titers. The egg albumin skin test was carried out at six weeks. Results of these studies are as follows:

TABLE 7

| Delayed Hypersensitivity and Antibody Production | | | | |
|---|---|---|---|---|
| | Antibody Titers | | DH | |
| TEST COMPOSITION | $Ab_3$ | $Ab_6$ | Diam. | Inf. |
| First | 3.83 | 7.50 | 15.16 | 2.33 |
| Second | 3.14 | 6.14 | 14.14 | 2.07 |
| Third | 1.85 | 5.42 | 10.64 | 1.29 |
| Fourth | 3.42 | 7.85 | 13.35 | 1.64 |
| Fifth | 2.83 | 5.33 | 10.75 | 1.33 |
| Sixth | 2.33 | 5.00 | 11.00 | 1.33 |

$Ab_3$ — Antibody titer level at 3 weeks.
$Ab_6$ — Antibody titer level at 6 weeks.
DH — Delayed hypersensitivity.
Diam. — Diameter of reaction in mm.
Inf. — Infiltration, scored on a scale of 1-3.

EXAMPLE 2

The effect of squalene on antibody activity was determined in the experiment set forth below. The procedure described in Example 1 was used in this study.

TABLE 8

| Components | Quantity |
|---|---|
| N—acetylmuramyl-L-Thr-D-Iglu | 250 μg |
| TWEEN ® 80 | 2 μl |
| PLURONIC ® L-121 | 25 μl |
| Squalene | 50 μl |
| PBS to | 1000 μl |

TABLE 9

| Components | Quantity |
|---|---|
| N—acetylmuramyl-L-Thr-D-Iglu | 250 μg |
| TWEEN ® 80 | 2 μl |
| PLURONIC ® L-121 | 25 μl |
| PBS to | 1000 μl |

TABLE 10

| Components | Quantity |
|---|---|
| TWEEN ® 80 | 2 μl |
| PLURONIC ® L-121 | 25 μl |
| PBS to | 1000 μl |

Egg albumin was mixed with the above formulations and 0.2 ml injected (S.C.) per guinea pig. A booster injection of egg albumin was given at 4 weeks. Animals were bled at 4 and 6 weeks to determine antibody titres, and skin tested with egg albumin at 6 weeks to measure delayed hypersensitivity. The results of these studies are as follows:

TABLE 11

| Delayed Hypersensitivity and Antibody Production | | | | |
|---|---|---|---|---|
| Test | Antibody Titers | | DH | |
| Composition | $Ab_4$ | $Ab_6$ | Diam. | Inf. |
| First | 5.00 ± 0.37 | 8.25 ± 0.31 | 17.70 ± 1.12 | 1.94 |

TABLE 11-continued

| Delayed Hypersensitivity and Antibody Production | | | | |
|---|---|---|---|---|
| Test | Antibody Titers | | DH | |
| Composition | $Ab_4$ | $Ab_6$ | Diam. | Inf. |
| Second | 2.87 ± 0.22 | 6.62 ± 0.26 | 12.37 ± 0.88 | 1.38 |
| Third | 2.12 ± 0.22 | 6.00 ± 0.33 | 10.25 ± 0.84 | 1.00 |

See Table 7 for the definition of the abbreviations.

EXAMPLE 3

Groups of 6 or 7 female guinea pigs, 400–500 g, were immunized with 200 μg of egg albumin (EA) in one of 4 vehicles. The basic vehicle mixture consisted of 0.2 ml of phosphate buffered saline with 0.2% TWEEN ®80 containing 10 μl of squalene (SQE) or squalane (SQA) and 5 μl of PLURONIC ®L-121. Two test groups were also given 50 μg/animal of the glycodipeptide N-acetylmuramyl-L-α-aminobutyryl-D-isoglutamine. The animals were boosted with 50 μg EA in saline on Day 28. On days 21, 35, and 50 the animals were bled by heart puncture and the sera assayed using the passive hemagglutination technique. On days 35 and 50 the animals were also skin tested with 10 μg EA injected ID. The skin tests were measured at 24 hours. The data obtained in this experiment are summarized in Table 12.

From the observations in these three Examples, it is is clear that to elicit a powerful cell mediated and humoral response, the combination of glycopeptide and PLURONIC ® polyol is essential. While these two components are essential, cell mediated and humoral response can be maximized by employing a metabolizable oil.

TABLE 12

DELAYED HYPERSENSITIVITY AND ANTIBODY PRODUCTION

| | Antibody Titers | | | DH | | | |
|---|---|---|---|---|---|---|---|
| | | | | 35 Days | | 49 Days | |
| | $Ab_3$ | $Ab_5$ | $Ab_7$ | Diam. | Inf. | Diam. | Inf. |
| PBS Control | 2.18 ± .17 | 2.83 ± .31 | 2.83 ± .31 | 6.17 ± 2.31 | 1.17 | 3.67 + 1.66 | 1.00 |
| L-121 Control | 2.00 ± .00 | 4.86 ± .74 | 5.57 ± .30 | 9.00 ± 1.61 | 1.14 | 8.00 ± 1.39 | 1.14 |
| SQE/Glycodipeptide | 2.43 ± .37 | 7.43 ± .48 | 7.83 ± .31 | 17.77 ± 1.38 | 2.14 | 12.50 ± 1.29 | 1.64 |
| SQA/Glycodipeptide | 2.29 ± .18 | 6.67 ± .42 | 7.83 ± .31 | 18.83 ± 0.71 | 2.33 | 13.83 ± 0.80 | 1.92 |

Infiltration Score: Infiltration is scored from 1(none) to 3(strongly infiltrated).

What is claimed is:

1. An adjuvant composition comprising:
   (a) an immunopotentiating amount of an immunostimulating glycopeptide, wherein said glycopeptide is a compound of the formula $$\text{(I)}$$

$$\begin{array}{c} CH_2OR \\ O \\ R^4R^1O \quad OR^3 \\ C \quad NHCOR^2 \\ H \quad C-XNHCH-(CH_2)_n R^6 \\ \| \quad \backslash \\ O \quad R^5 \end{array}$$

wherein R and $R^1$ are the same or different and are hydrogen or acyl containing from 1 to 22 carbon atoms;

$R^2$ is an unsubstituted or substituted alkyl radical containing from 1 to 22 carbon atoms, or a unsubstituted or substituted aryl radical containing from 6 to 10 carbon atoms;

$R^3$ is hydrogen, alkyl, or aryl of 7 to 10 carbon atoms;

$R^4$ is hydrogen or alkyl;

X is an aminoacyl moiety selected from the group consisting of alanyl, valyl, leucyl, isoleucyl, α-aminobutyryl, threonyl, methionyl, cysteinyl, glutamyl, glutaminyl, aspartyl, phenylalanyl, tyrosyl, tryptophanyl, lysyl, ornithinyl, arginyl, histidyl, asparginyl, prolyl, hydroxyprolyl, seryl, or glycyl;

$R^5$ and $R^6$ are the same or different and are a carboxyl group, a carboxyl group esterified with a lower alkanol, or a carbamoyl group, which, on the nitrogen atom, is unsubstituted or mono-substituted or di-substituted by alkyl, aryl, aralkyl, alkylidene, or carbamoylmethyl;

(b) a multi-phase-forming amount between 0.2 and 49% by volume (v/v) of a non-toxic polyoxypropylene-polyoxyethylene block polymer, wherein said block polymer is liquid over a temperature range between about 15°–40° C., has a polyoxypropylene base of molecular weight between 2250 and 4300, and has polyoxyethylene in an amount between 1 and 30% of the block polymer;

(c) a multi-phase-stabilizing amount between 0.05 and 2.5% by volume (v/v) of a glycol ether-based surfactant; and (d) buffered isoosmotic saline in a quantity sufficient to make volume.

2. The composition of claim 1 wherein said glycopeptide is present in an amount between 0.01 to 2% by weight/volume.

3. An adjuvant composition comprising:

(a) an immunopotentiating amount of an immunostimulating glycopeptide, wherein said glycopeptide is a compound of the formula

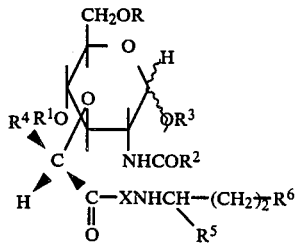

(I)

wherein R and $R^1$ are the same or different and are hydrogen or acyl containing from 1 to 22 carbon atoms;

$R^2$ is unsubstituted or substituted alkyl radical containing from 1 to 22 carbon atoms, or an unsubstituted or substituted aryl radical containing from 6 to 10 carbon atoms;

$R^3$ is hydrogen, alkyl, or aryl of 7 to 10 carbon atoms;

$R^4$ is hydrogen or alkyl;

X is an aminoacyl moiety selected from the group consisting of alanyl, valyl, leucyl, isoleucyl, α-aminobutyryl, threonyl, methionyl, cysteinyl, glutamyl, glutaminyl, aspartyl, phenylalanyl, tyrosyl, tryptophanyl, lysyl, ornithinyl, arginyl, histidyl, asparginyl, prolyl, hydroxyprolyl, seryl, or glycyl;

$R^5$ and $R^6$ are the same or different and are a carboxyl group, a carboxyl group esterified with a lower alkanol, or a carbamoyl group, which, on the nitrogen atom, is unsubstituted or mono-substituted or di-substituted by alkyl, aryl, aralkyl, alkylidene, or carbamoylmethyl;

(b) a multi-phase-forming amount between 0.2 and 49% by volume (v/v) of a non-toxic polyoxypropylene-polyoxyethylene block polymer, wherein said block polymer is liquid over a temperature range between about 15°–40° C., has a polyoxypropylene base of molecular weight between 2250 and 4300, and has polyoxyethylene in an amount between 1 and 30% of the block polymer;

(c) a multi-phase-stabilizing amount between 0.05 and 2.5% by volume (v/v) of a glycol ether-based surfactant;

(d) a metabolizable, non-toxic oil in an amount between 1 to 30% by volume (v/v); and (e) buffered isoosmotic saline in a quantity sufficient to make volume.

4. The composition of claim 3 wherein said glycopeptide is present in an amount between 0.01 to 2% by weight/volume.

5. The composition of claim 2 wherein said block polymer is comprised of a polyoxypropylene base of molecular weight between 3,250 and 4,000 and polyoxyethylene in an amount between 0.2 and 20% of said block polymer; and said saline is phosphate buffered saline.

6. The composition of claim 5 wherein the glycopeptide is a compound of Formula (I) wherein R and $R^1$ are the same or different and are selected from the group consisting of hydrogen or an acyl radical containing from 1 to 22 carbon atoms;

$R^2$ is methyl;

$R^3$ is hydrogen;

X is present in an amount between 0.01 and 1% (w/v) and is an aminoacyl moiety selected from the group consisting of L-seryl, L-alanyl, L-valyl, L-leucyl, L-isoleucyl, L-α-aminobutyryl, L-threonyl, L-methionyl, L-cysteinyl, L-phenylalanyl, L-tyrosyl, L-tryptophanyl, L-lysyl, L-ornithyl, L-arginyl, L-histidyl, L-glutamyl, L-glutaminyl, L-aspartyl, L-asparaginyl, L-prolyl, or L-hydroxyprolyl;

said block polymer is prsent in an amount between 0.2 and 20% (v/v) and is comprised of polyoxypropylene base of molecular weight between 2,750 and 3,550 and polyoxyethylene in an amount between 5 and 20% of said block polymer; and said glycol ether-based surfactant is a polysorbate surfactant present in an amount between 0.2 and 1% (v/v).

7. The composition of claim 6 wherein said glycopeptide is a compound of Formula (I) wherein R, $R^1$ and $R^3$ are hydrogen;

$R^2$ is methyl;

$R^4$ is methyl or hydrogen;

X is L-valyl, L-alanyl, L-seryl, L-threonyl or L-α-aminobutyryl;

$R^5$ is carboxyl, carbamoyl or n-butyl carboxylate; and $R^6$ is carboxyl or carbamoyl.

8. The composition of claim 7 wherein said glycopeptide is N-acetylmuramyl-L-threonyl-D-isoglutamine, N-acetyl-L-α-aminobutyryl-D-isoglutamine, 6-O-stearoyl-N-acetylmuramyl-L-α-aminobutyryl-D-isoglutamine, or N-acetyldesmethylmuramyl-L-alanyl-D-isoglutamine present in an amount between 0.01 to 1% (w/v);

said block polymer is present in an amount between 0.2 and 5% (v/v) and is comprised of a polyoxypropylene base of molecular weight 3250 and polyoxyethylene in an amount of 10% of said block polymer; and said polysorbate surfactant is polyoxyethylene 20 sorbitan monooleate.

9. The composition of claim 7 wherein said glycopeptide is n-butyl-N-acetylmuramyl-L-alanyl-D-glutaminate, N-acetylmuramyl-L-alanyl-D-isoglutamine, or N-acetylmuramyl-L-seryl-D-isoglutamine; and said block polymer is comprised of a polyoxypropylene base of molecular weight 3250 and polyoxyethylene in an amount of 10% of said block polymer.

10. The composition of claim 8 wherein said glycopeptide is N-acetylmuramyl-L-threonyl-D-isoglutamine present in an amount of 0.5% (w/v), and said block polymer is present in an amount of 2.5% (v/v).

11. The composition of claim 4 wherein said block polymer is comprised of a polyoxypropylene base of molecular weight between 3,250 and 4,000 and polyoxyethylene in an amount between about 0.2 and 20% of said block polymer; and said saline is phosphate buffered saline.

12. The composition of claim 11 wherein the glycopeptide of Formula (I) wherein

R and $R^1$ are the same or different and are selected from the group consisting of hydrogen or an acyl radical containing from 1 to 22 carbon atoms;

$R^2$ is methyl;

$R^3$ is hydrogen;

X is present in an amount between 0.01 and 1% (w/v) and is an aminoacyl moiety selected from the group consisting of L-seryl, L-alanyl, L-valyl, L-leucyl, L-isoleucyl, L-α-aminobutyryl, L-threonyl, L-methionyl, L-cysteinyl, L-phenylalanyl, L-tyrosyl, L-tryptophanyl, L-lysyl, L-ornithyl, L-arginyl, L-histidyl, L-glutamyl, L-glutaminyl, L-aspartyl, L-asparaginyl, L-prolyl, or L-hydroxyprolyl;

said block polymer is present in an amount between 0.2 and 20% (v/v) and is comprised of polyoxypropylene base of molecular weight between 2,750 and 3,550 and polyoxyethylene in an amount between 5 and 20% of said block polymer; and said glycol ether-based surfactant is a polysorbate surfactant present in an amount between 0.2 and 1% (v/v).

13. The composition of claim 12 wherein said glycopeptide is a compound of Formula (I) wherein R, $R^1$ and $R^3$ are hydrogen;

$R^2$ is methyl;

$R^4$ is methyl or hydrogen;

X is L-valyl, L-alanyl, L-seryl, L-threonyl or L-α-aminobutyryl;

$R^5$ is carboxyl, carbamoyl or n-butyl carboxylate; and $R^6$ is carboxyl or carbamoyl.

14. The composition of claim 13 wherein said glycopeptide is N-acetylmuramyl-L-threonyl-D-isoglutamine, N-acetyl-L-α-aminobutyryl-D-isoglutamine, 6-O-stearoyl-N-acetylmuramyl-L-α-aminobutyryl-D-isoglutamine, or N-acetyldesmethylmuramyl-L-alanyl-D-isoglutamine present in an amount between 0.01 and 1% (w/v);

said block polymer is present in an amount between 0.2 and 5% (v/v) and is comprised of a polyoxypropylene base of molecular weight 3250 and polyoxyethylene in an amount of 10% of said block polymer; and said polysorbate surfactant is polyoxyethylene 20 sorbitan monooleate.

15. The composition of claim 13 wherein said glycopeptide is n-butyl-N-acetylmuramyl-L-alanyl-D-glutaminate, N-acetylmuramyl-L-alanyl-D-isoglutamine, or N-acetylmuramyl-L-seryl-D-isoglutamine; and said block polymer is comprised of a polyoxypropylene base of molecular weight 3250 and polyoxyethylene in an amount of 10% of said block polymer.

16. A composition according to claim 8 wherein said glycopeptide is N-acetylmuramyl-L-threonyl-D-isoglutamine present in an amount of 0.5% (w/v), and said block polymer is present in an amount of 2.5% (v/v).

* * * * *